(12) United States Patent
Barker

(10) Patent No.: US 8,478,426 B2
(45) Date of Patent: Jul. 2, 2013

(54) SYSTEMS AND METHODS FOR MAKING AND USING ELECTRICAL STIMULATION SYSTEMS HAVING MULTI-LEAD-ELEMENT LEAD BODIES

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 111 days.

(21) Appl. No.: 13/185,078

(22) Filed: Jul. 18, 2011

(65) Prior Publication Data

US 2012/0029596 A1 Feb. 2, 2012

Related U.S. Application Data

(60) Provisional application No. 61/368,943, filed on Jul. 29, 2010.

(51) Int. Cl.
*A61N 1/00* (2006.01)

(52) U.S. Cl.
USPC .......................................................... 607/116

(58) Field of Classification Search
USPC ................................................ 607/115–132
See application file for complete search history.

(56) References Cited

U.S. PATENT DOCUMENTS

| | | | |
|---|---|---|---|
| 4,214,594 A | 7/1980 | Little et al. | |
| 6,006,139 A | 12/1999 | Kruse et al. | |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,031,774 B1 | 4/2006 | Doan et al. | |
| 7,244,150 B1 | 7/2007 | Brase et al. | |
| 7,672,734 B2 | 3/2010 | Anderson et al. | |
| 7,761,165 B1 | 7/2010 | He et al. | |
| 2003/0114905 A1 | 6/2003 | Kuzma | |
| 2005/0080470 A1* | 4/2005 | Westlund et al. | ............. 607/119 |
| 2005/0165465 A1 | 7/2005 | Pianca et al. | |
| 2007/0150036 A1 | 6/2007 | Anderson | |
| 2007/0219595 A1 | 9/2007 | He | |
| 2007/0239243 A1 | 10/2007 | Moffitt et al. | |
| 2008/0071320 A1 | 3/2008 | Brase | |

OTHER PUBLICATIONS

International Search Report and Written Opinion for International Patent Application No. PCT/US2011/044395 mailed Oct. 12, 2011.

\* cited by examiner

*Primary Examiner* — Scott Getzow

(74) *Attorney, Agent, or Firm* — Frommer Lawrence & Haug LLP; Patrick R. Turner

(57) ABSTRACT

A lead for providing electrical stimulation of patient tissue includes a distal lead element, at least two proximal lead elements, and a junction coupling the distal lead element to each of the at least two proximal lead elements. The distal lead element includes a plurality of electrodes and a plurality of conductive wires coupled to the plurality of electrodes and extending along a longitudinal axis of the distal lead element. Each of the at least two proximal lead elements includes a plurality of terminals and a plurality of conductive wires coupled to the plurality of terminals and extending along a longitudinal axis of the proximal lead element. The junction includes a circuit arrangement electrically coupling each of the conductive wires of the distal lead element to at least one of the conductive wires of at least one of the at least two proximal lead elements.

20 Claims, 11 Drawing Sheets

SYSTEMS AND METHODS FOR MAKING AND USING ELECTRICAL STIMULATION SYSTEMS HAVING MULTI-LEAD-ELEMENT LEAD BODIES

CROSS-REFERENCE TO RELATED APPLICATIONS

This application claims the benefit under 35 U.S.C. §119(e) of U.S. Provisional Patent Application Ser. No. 61/368,943 filed on Jul. 29, 2010, which is incorporated herein by reference.

FIELD

The present invention is directed to the area of implantable electrical stimulation systems and methods of making and using the systems. The present invention is also directed to implantable electrical stimulation leads having lead bodies with multiple lead elements coupled to one another via circuit arrangements, as well as methods of making and using the leads, lead bodies, lead elements, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead for providing electrical stimulation of patient tissue includes a distal lead element, at least two proximal lead elements, and a junction coupling the distal lead element to each of the at least two proximal lead elements. The distal lead element includes a plurality of electrodes and a plurality of conductive wires coupled to the plurality of electrodes and extending along a longitudinal axis of the distal lead element. Each of the at least two proximal lead elements includes a plurality of terminals and a plurality of conductive wires coupled to the plurality of terminals and extending along a longitudinal axis of the proximal lead element. The junction includes a circuit arrangement electrically coupling each of the conductive wires of the distal lead element to at least one of the conductive wires of at least one of the at least two proximal lead elements.

In another embodiment, a method of fabricating a lead includes providing a plurality of electrodes on a distal lead element, providing a plurality of first terminals on a first proximal lead element, and providing a plurality of second terminals on a second proximal element. A plurality of conductive wires are electrically coupled to the plurality of electrodes and are extended along a longitudinal length of the distal lead element. A plurality of conductive wires are electrically coupled to the plurality of first terminals and are extended along a longitudinal length of the first proximal lead element. A plurality of conductive wires are electrically coupled to the plurality of second terminals and are extended along a longitudinal length of the second proximal lead element. Each of the conductive wires of the distal lead element are electrically coupled to at least one of the conductive wires of either of the first proximal lead element or the second proximal lead element using a circuit arrangement. The circuit arrangement is inserted into a junction. The distal lead element, the first proximal lead element and the second proximal lead element are coupled to the junction.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having lead bodies with multiple lead elements coupled to one another via circuit arrangements, as well as methods of making and using the leads, lead bodies, lead elements, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; and 7,761,165; and U.S. Patent Applications Publication Nos. 2003/0114905, 2005/0165465, 2007/0150036; 2007/0219595; 2007/0239243; and 2008/0071320, all of which are incorporated by reference.

Figure 1:
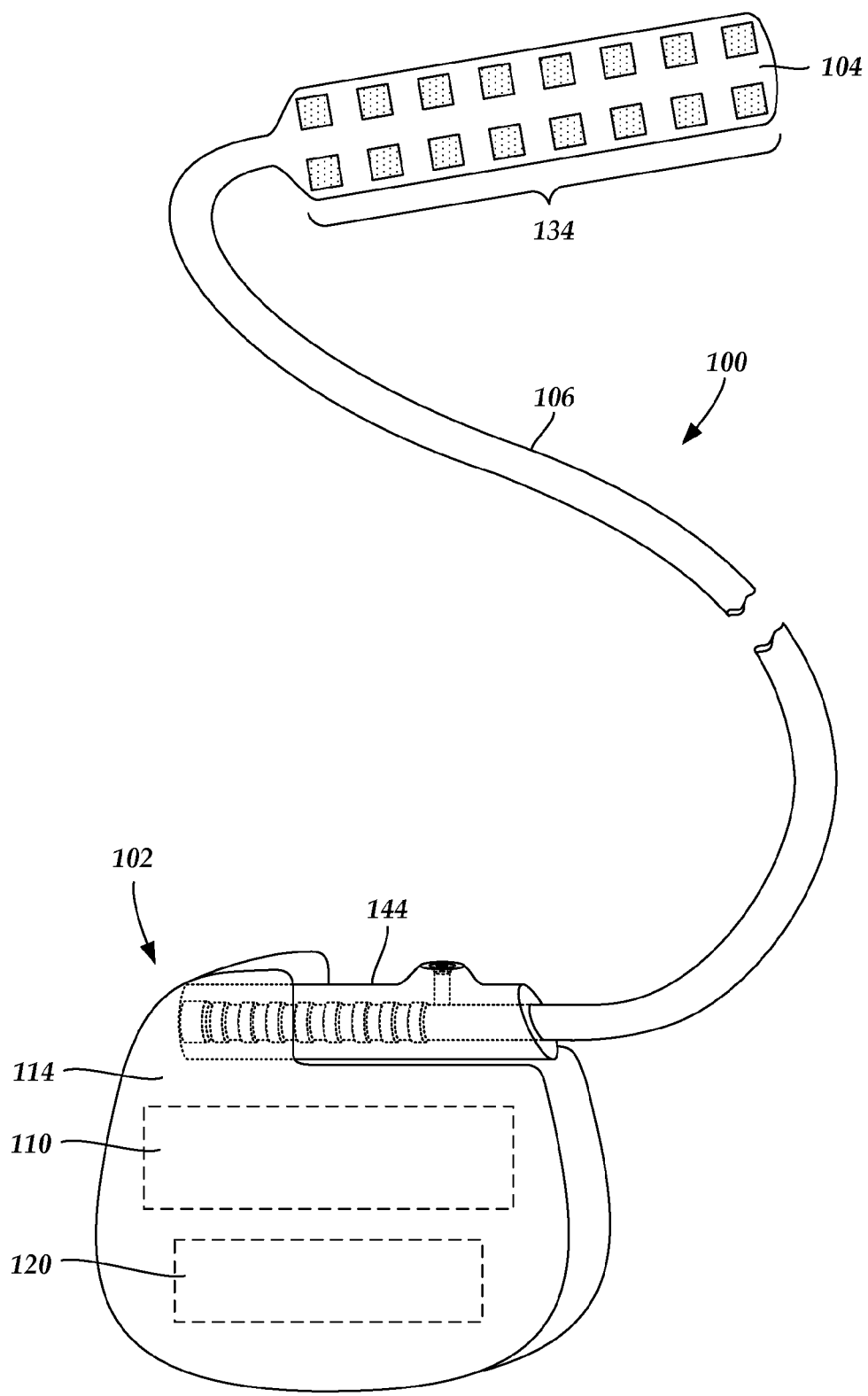
FIG. 1 is a schematic view of one embodiment of an electrical stimulation system, according to the invention.
Figure 2:
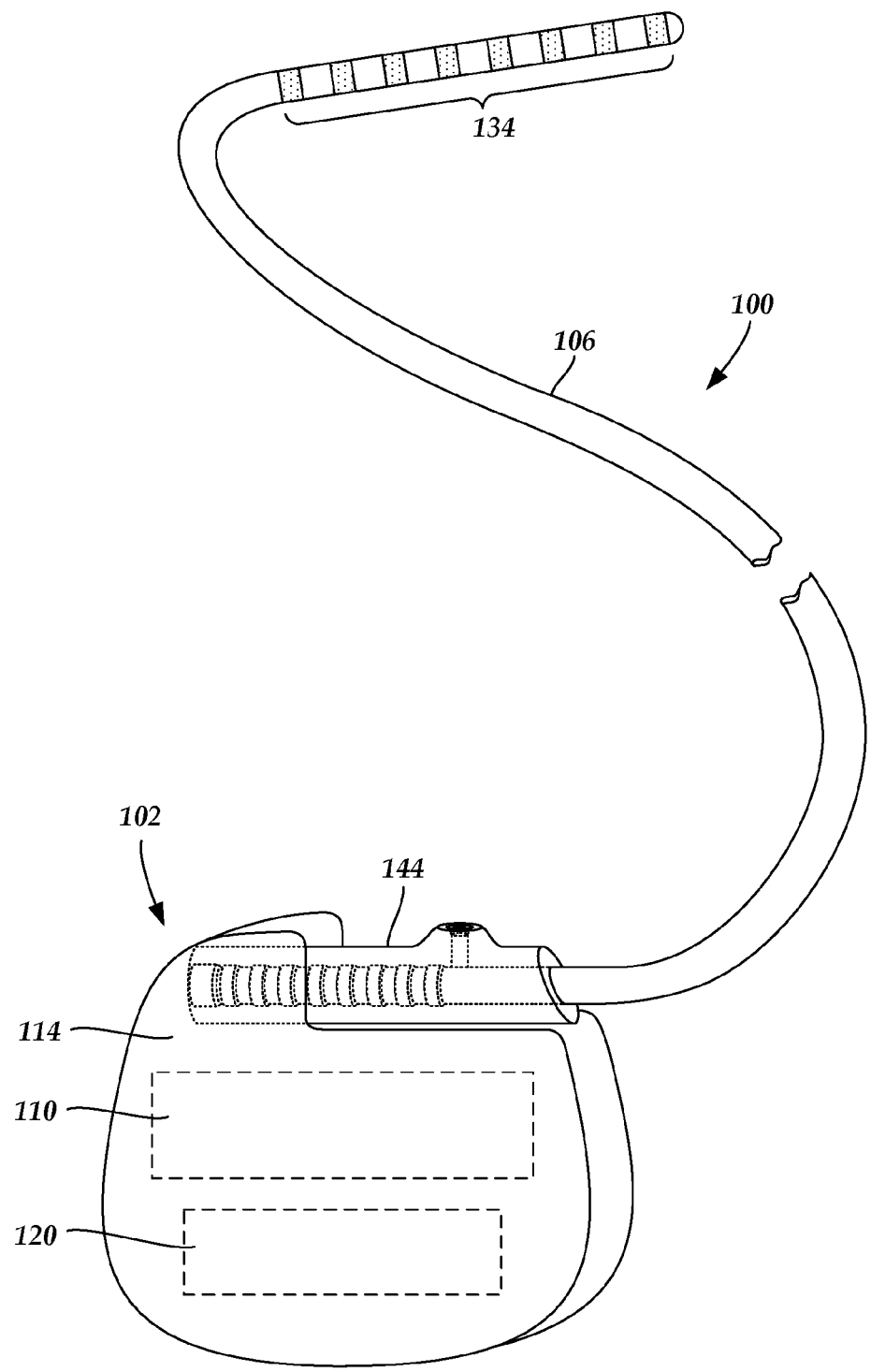
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
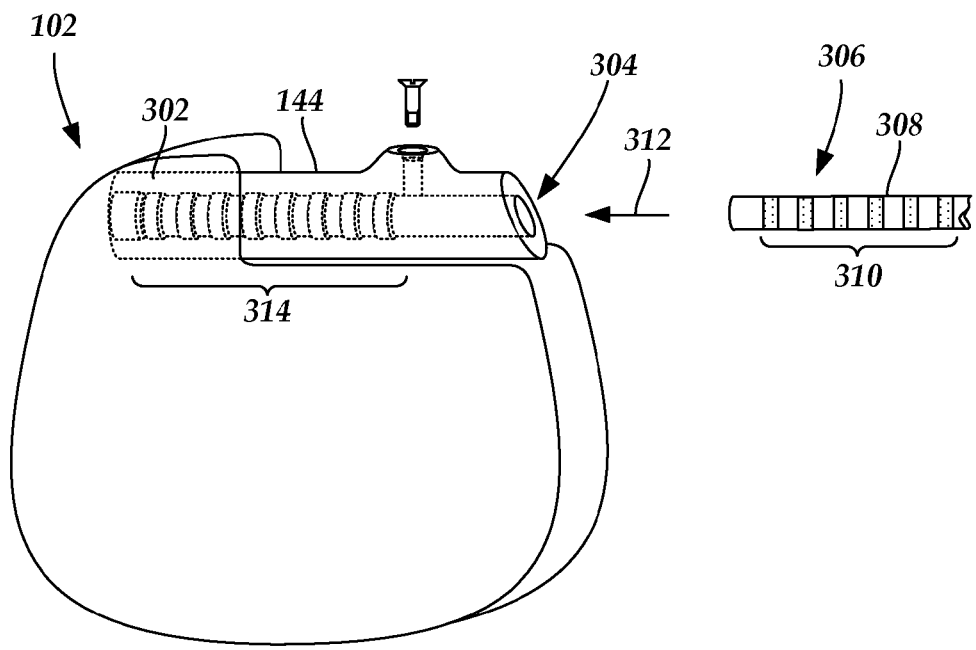
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
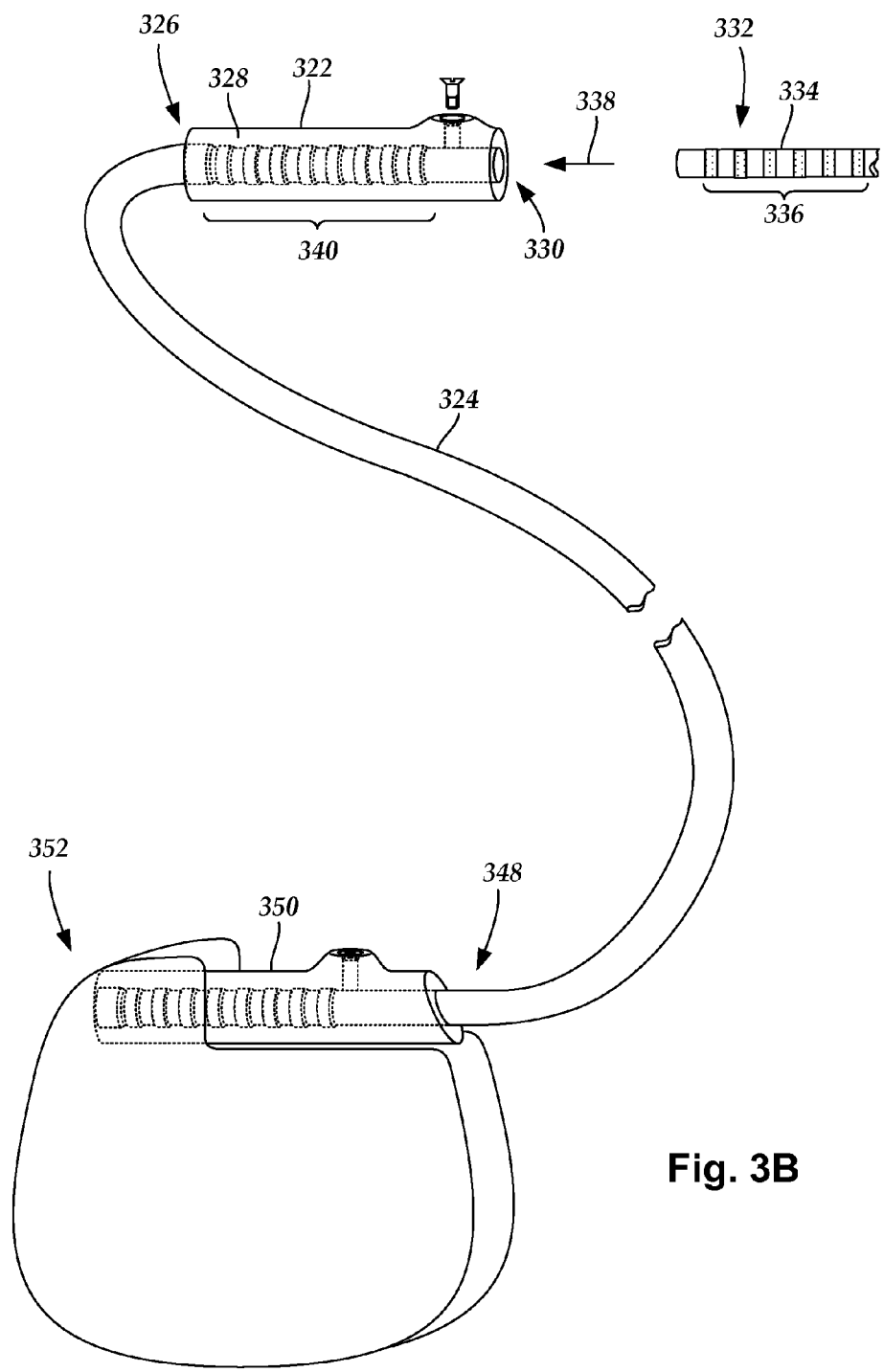
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

In at least some embodiments, the lead includes a lead body having a plurality of lead elements, a "multi-lead-element lead body." The multi-lead-element lead body includes a distal lead element and one or more proximal lead elements. The distal lead element is coupled to the one or more proximal lead elements via a junction. A plurality of electrodes are disposed on the distal lead element. A plurality of conductive wires are electrically coupled to the electrodes and extend along the distal lead element to the junction. A plurality of terminals are disposed one each of the proximal lead elements. A plurality of conductive wires are electrically coupled to the terminals and extend along the proximal lead elements to the junction. A circuit arrangement is disposed in the junction and electrically couples the conductive wires of the distal lead element to one or more conductive wires of one or more proximal lead elements. In at least some embodiments, the circuit arrangement is configured and arranged to roll up.

As described above, in at least some embodiments the electrodes are configured and arranged for implantation into an epidural space of a patient. In at least some embodiments, the terminals are configured and arranged for insertion into a connector disposed on, for example, a control module, a lead extension, an operating room cable, an external trial stimulator, or the like or combinations thereof. It will be understood that the multi-lead-element lead body may be used with many different lead configurations, including a paddle lead (see e.g., FIG. 1) or a percutaneous lead (see e.g., FIG. 2).

It may be an advantage to couple a distal lead element to one or more proximal lead elements via a junction because it may increase manufacturing flexibility. For example, the lead can be manufactured with any number of lead elements. Also, lead elements can be manufactured with different lengths, widths, terminal or electrode arrangements, or the like. It may also reduce cost, for example, by enabling malfunctioning portions of the lead to be replaced without replacing the entire lead. Another reason for manufacturing the lead in separate elements is to allow center-less grinding of each contact array (e.g., terminals and electrodes) before joining the elements together at the junction, otherwise the junction and other two proximal lead elements may flop around in the grinder during grinding of each array if pre-joined.

Figure 4:
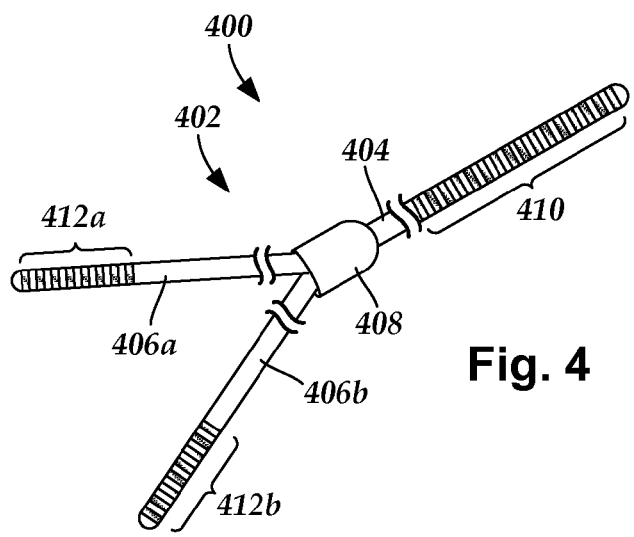
FIG. 4 is a schematic perspective view of one embodiment of a lead with a lead body that includes a distal lead element coupled to proximal lead elements via a junction, according to the invention.

FIG. 4 is a schematic perspective view of one embodiment of a lead 400 that includes a multi-lead-element lead body 402. The multi-lead-element lead body 402 includes a distal lead element 404 and proximal lead elements 406a and 406b. The distal lead element 404 is coupled to the proximal lead elements 406a and 406b via a junction 408. In at least some embodiments, a plurality of electrodes 410 are disposed on the distal lead element 404. In at least some embodiments, a plurality of terminals 412a and 412b are disposed on one or more of the proximal lead elements 406a and 406b, respectively. In at least some embodiments, the lead 400 is configured and arranged for attachment to a conventional implantable pulse generator.

The distal and proximal lead elements can be any length. In preferred embodiments, the distal lead element is longer than the one or more proximal lead elements. In at least some embodiments, however, the one or more proximal lead elements are at least as long as the distal lead element. In at least some embodiments, when the lead body includes multiple proximal lead elements, at least two of the proximal lead elements have different lengths from one another. In at least some embodiments, each of the lead elements have equal diameters. In at least some embodiments, the distal lead element has a larger diameter than the one or more proximal lead elements. In at least some other embodiments, the distal lead element has a smaller diameter than the one or more proximal lead elements.

In at least some embodiments, a circuit arrangement is disposed in the junction 408. In at least some embodiments, the electrodes 410 are electrically coupled to the one or more of the terminals 412a or 412b via the circuit arrangement. In at least some embodiments, the circuit arrangement can be rolled or folded up and inserted into the junction 408 (e.g., a molded portion of the junction 408, or the like).

Figure 5:
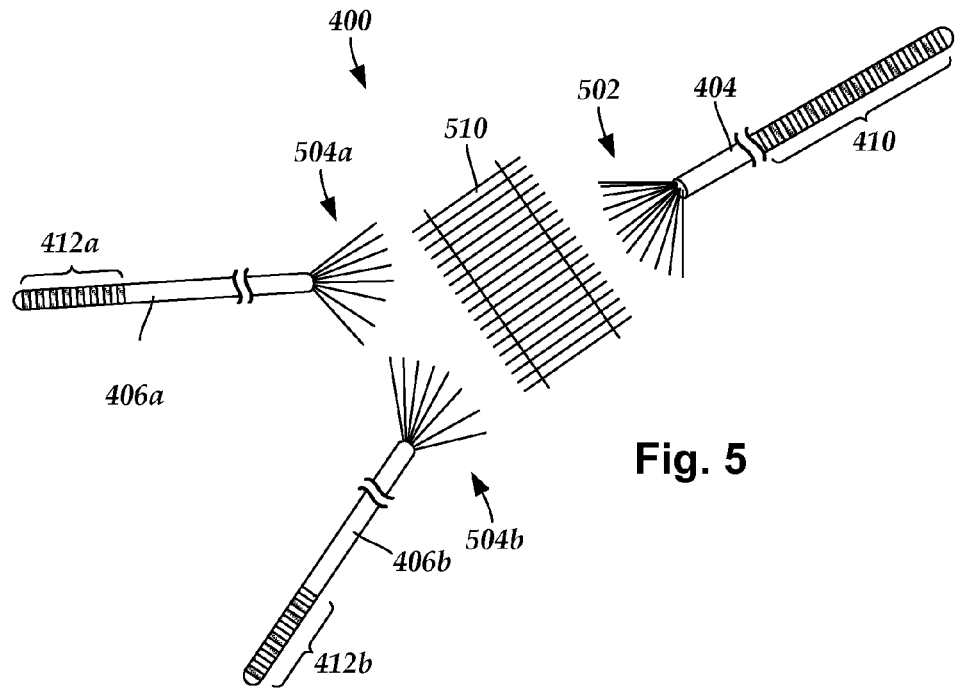
FIG. 5 is a schematic perspective exploded view of one embodiment of the lead of FIG. 4, the lead including a circuit arrangement to which conductive wires extending from the lead elements of FIG. 4 are coupleable, according to the invention.

FIG. 5 is a schematic perspective exploded view of one embodiment of the lead 400. The distal lead element 404 includes a plurality of conductive wires 502 coupled to the electrodes 410 and extending along a longitudinal axis of the distal lead element 404 to a proximal end of the distal lead element 404. In FIG. 5, the conductive wires 502 are shown extending outwardly from the proximal end of the distal lead element 404. The proximal lead element 406a includes a plurality of conductive wires 504a coupled to the terminals 412a and extending along a longitudinal axis of the proximal lead element 406a to a distal end of the proximal lead element 406a. In FIG. 5, the conductive wires 504a are shown extending outwardly from the distal end of the proximal lead element 406a. Similarly, the proximal lead element 406b includes a plurality of conductive wires 504b coupled to the terminals 412b and extending along a longitudinal axis of the proximal lead element 406b to a distal end of the proximal lead element 406b. In FIG. 5, the conductive wires 504b are shown extending outwardly from the distal end of the proximal lead element 406b.

A circuit arrangement 510 is disposed between the conductive wires 502, 504a, and 504b. As discussed above, the circuit arrangement 510 electrically couples each of the conductive wires 502 to one or more of the conductive wires 504a or 504b. In at least some embodiments, the number of conductive wires 502 is equal to the number of electrodes 410. In at least some embodiments, the number of conductive wires 502 is equal to the number of conductive wires 504a plus the number of conductive wires 504b. In at least some embodiments, the number of conductive wires 504a is equal to the number of terminals 412a. In at least some embodiments, the number of conductive wires 504b is equal to the number of terminals 412b. In at least some embodiments, the number of conductive wires 504a is equal to the number of conductive wires 504b. In at least some embodiments, one or more of the conductive wires 502, 504a, or 504b differ in diameter, materials, or configuration from at least one other of the conductive wires 502, 504a, or 504b. In at least some embodiments, each of the conductive wires 502, 504a, or 504b are equivalent in at least one of diameter, materials, or configuration from at least one other of the conductive wires 502, 504a, or 504b. In at least some embodiments, each individual conductive wire 502 couples to one and only one of the conductive wires 504a, 504b.

In at least some embodiments, the number of electrodes 410 is equal to the number of the terminals 412a plus the number of the terminals 412b. In at least some embodiments, the number of terminals 412a is equal to the number of terminals 412b. The distal lead element 404 can include any number of electrodes including, for example, two, three, four, five, six, seven, eight, nine, ten, eleven, twelve, fourteen, sixteen, twenty, twenty-four, thirty-two, forty, or more electrodes. The proximal lead elements 406a and 406b can include any number of terminals including, for example, one, two, three, four, five, six, seven, eight, nine, ten, eleven, twelve, fourteen, sixteen, or more terminals.

Figure 6:
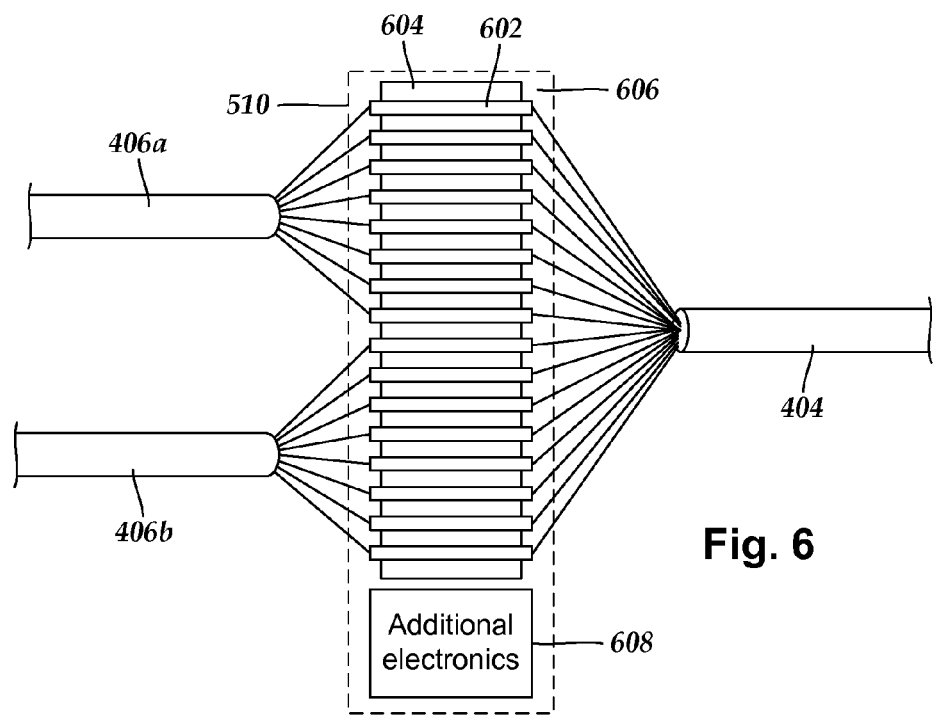
FIG. 6 is a schematic side view of one embodiment of the circuit arrangement of FIG. 5 coupling conductive wires of the distal lead element of FIG. 4 to conductive wires of the proximal lead elements of FIG. 5, according to the invention.

FIG. 6 is a schematic side view of one embodiment of the conductive wires 502, 504a, and 504b coupled to the circuit arrangement 510, which is laid out in a relatively flat configuration. In at least some embodiments, the circuit arrangement 510 includes an array of conductive junction elements 602 embedded within a non-conductive flexible substrate 604. In at least some embodiments, the conductive junction elements 602 are stamped or laser cut. In at least some embodiments, the flexible substrate 604 on which the conductive junction elements 602 are embedded is a polymer sheet (e.g., silicone, or the like).

In at least some embodiments, conductive junction elements 602 include one or more tracings. In at least some embodiments, the conductive junction elements 602 include one or more conductive struts. In at least some embodiments, an insulating jacket 606 is disposed over at least one of the circuit arrangement 510 or the junction 408. In at least some embodiments, the insulating jacket 606 includes one or more adhesive strips for holding one or more of the conductive junction elements 602 in place.

In alternate embodiments, the circuit arrangement 510 includes a printed circuit disposed on a flexible substrate, or a "flex circuit." In at least some embodiments, the flexible substrate on which the printed circuit arrangement is disposed is formed from polyimide.

The junction 408 optionally houses one or more additional electrical components 608 including, for example, one or more biosensors, a telemetry unit, a signal conditioning unit, or the like. In at least some embodiments, the one or more additional electrical components 608 are at least partially disposed on the circuit arrangement 510.

The conductive wires 502, 504a, and 504b can be coupled to the circuit arrangement 510 in any manner. In preferred embodiments, the conductive wires 502, 504a, and 504b are resistance welded or laser welded to the circuit arrangement 510. In other embodiments, the conductive wires 502, 504a, and 504b are crimped, soldered, or the like, to the circuit arrangement 510. It may be an advantage to resistance weld the conductive wires 502, 504a, and 504b to the circuit arrangement 510 so that ends of the conductive wires 502, 504a, and 504b do not need to be ablated prior to coupling the conductive wires to the circuit arrangement. It may be an advantage to laser weld the conductive wires 502, 504a, and 504b to the circuit arrangement 510 so that welding can be performed as an automated, or semi-automated, process.

Figure 7:
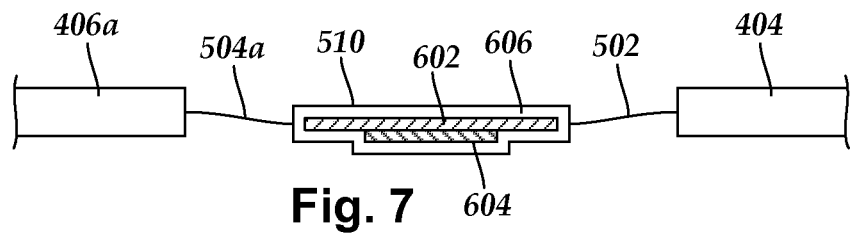
FIG. 7 is a schematic longitudinal cross-sectional view of one embodiment of the distal lead element of FIG. 4 coupled to one of the proximal lead elements of FIG. 4 via the circuit arrangement of FIG. 5, according to the invention.

FIG. 7 is a schematic longitudinal cross-sectional view of one embodiment of one of the conductive wires 502 coupled to one of the conductive wires 504a, via the circuit arrangement 510. In FIG. 7, the conductive wires 502 and 504a are shown coupled to opposite ends of one of the conductive struts 602. It will be understood that the conductive wires 502 and 504 can be coupled anywhere along one of the conductive struts 602.

Figure 8:
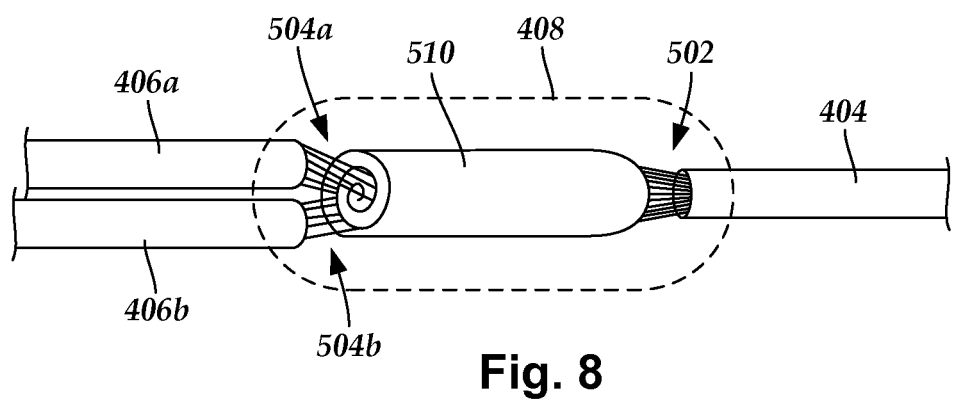
FIG. 8 is a schematic perspective view of one embodiment of the circuit arrangement of FIG. 5 coupling conductive wires from the distal lead element of FIG. 4 to conductive wires of the proximal lead elements of FIG. 4, the circuit arrangement rolled up and disposed in a junction, according to the invention.
Figure 9:
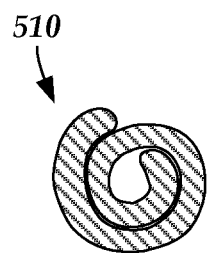
FIG. 9 is a schematic transverse cross-sectional view of one embodiment of the rolled up circuit arrangement of FIG. 8, according to the invention.

FIG. 8 is a schematic perspective close-up view of one embodiment of the conductive wires 502 coupled to one or more of the conductive wires 504a and 504b via the circuit arrangement 510. The circuit arrangement 510 is rolled up and disposed in the junction 408, which is shown transparently in FIG. 8 bounded by a dashed line, for clarity of illustration. FIG. 9 is a schematic transverse cross-sectional view of one embodiment of the rolled-up circuit arrangement 510.

Rolling up the circuit arrangement 510 may reduce the profile of the circuit arrangement 510, thereby reducing the profile of the junction 408. In at least some embodiments, the rolled-up circuit arrangement 510 is potted within the junction 408. In at least some embodiments, the rolled-up circuit arrangement 510 is potted with a hard, biocompatible resin (e.g., polyurethane, silicone adhesive, epoxy, or the like) using, for example, a casting mold. In at least some embodiments, the resin has a dielectric constant of at least 2. For example, in at least some embodiments, a resin formed from polyimide may have a dielectric constant of approximately 2.8. As another example, in at least some embodiments a resin formed from silicone rubber may have a dielectric constant of approximately 3 to 10.

It may be an advantage to pot the circuit arrangement 510 with a hard resin to provide strain relief for the lead elements 404, 406a, and 406b extending from the junction 408. Providing strain relief for the lead elements 502, 504a, and 504b extending from the junction 408, may reduce, or even eliminate, transmission of tensile/flex loading to points of connection between the conductive wires 502, 504a, and 504b and the circuit arrangement 510 (e.g., weld joints, or the like).

In at least some embodiments, the conductive wires 502, 504a, and 504b are coupled to the circuit arrangement 510 after the conductive wires 502 are coupled to the electrodes 410 and the conductive wires 504a and 504b are coupled to the terminals 412a and 412b, respectively. In at least some embodiments, center-less grinding may be performed on one or more of the lead elements 404, 406a, or 406b prior to coupling the lead elements 404, 406a, and 406b to the junction 408.

As mentioned above, the multi-lead-element lead body 402 can be used with either a percutaneous lead or a paddle lead. When the multi-lead-element lead body 402 is used in conjunction with a percutaneous lead, the lead may be introduced into a patient using an epidural needle. In at least some embodiments, a stylet may be used to facilitate guidance of the lead within the patient. In at least some embodiments, a transition tube may be employed to receive the stylet within the junction 408.

Figure 10:
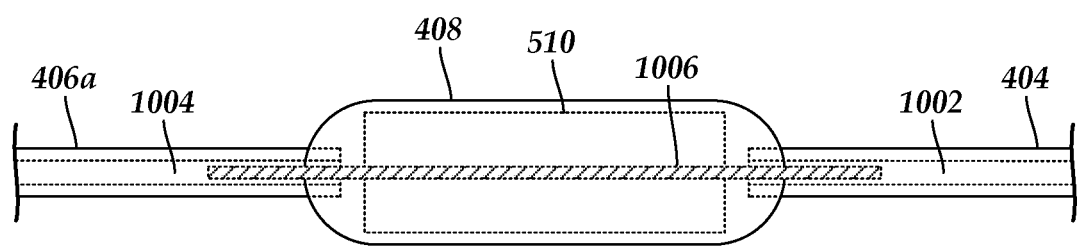
FIG. 10 is a schematic longitudinal transverse cross-sectional view of one embodiment of a transition tube extending through the junction of FIG. 4 from a lumen of the distal lead element of FIG. 4 to a lumen of one of the proximal lead elements of FIG. 4, according to the invention.

FIG. 10 is a schematic longitudinal cross-sectional view of one embodiment of the distal lead element 404, the proximal lead element 406a, and the junction 408 therebetween. A lumen 1002 is defined along a longitudinal axis of the distal lead element. A lumen 1004 is defined along a longitudinal axis of the proximal lead element 406a. A transition tube 1006 extends through the junction 408 from the lumen 1002 extending within the distal lead element 404 to the lumen 1004 extending within the proximal lead element 406a. In at least some embodiments, the transition tube 1006 enables passage of a stylet through both the proximal lead element 406a and the distal lead element 404. The stylet may provide stiffness to the lead to facilitate at least one of insertion, steering, or implantation of the lead. It will be understood that the conductive wires 502, 504a, and 504b are omitted from FIG. 10, for clarity of illustration.

Figure 11:
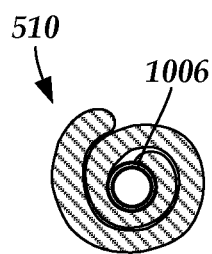
FIG. 11 is a schematic transverse cross-sectional view of one embodiment of the transition tube of FIG. 10 extending through the rolled up circuit arrangement of FIG. 8, according to the invention.

In at least some embodiments, the transition tube 1006 is rolled up within the circuit arrangement 510 (see e.g., FIG. 11). In at least some embodiments, the transition tube 1006 is rolled up within the circuit arrangement 510 when the junction 408 is potted. Once the ends of the transition tube 1006 are coupled to the lumen 1002 of the distal lead element 404 and the lumen 1004 of the proximal lead element 406a, a stylet may be introduced into an access port (not shown) in the proximal lead element 406a and advanced through the lumen 1004 of the proximal lead element 406a, the transition tube 1006 of the junction 408, and into the lumen 1002 of the distal lead element 404.

At least some leads, such as the lead shown in FIG. 2, are isodiametric to facilitate sliding of an epidural needle over a proximal end of the trial stimulation lead during removal of the epidural needle from a patient once the lead is positioned within a patient. In at least some embodiments, the junction 408 (as shown in FIGS. 4 and 8) has a circumference that is larger than a circumference of at least one of the distal lead element 404, the proximal lead element 406a, or the proximal lead element 406b. In at least some embodiments, the collective diameter of the proximal lead element 406a and the proximal lead element 406b is larger than the diameter of the distal lead element 404. Thus, the larger-sized junction 408 (or the collective diameter of a plurality of proximal lead elements) may hinder, or even prevent, a conventional epidural needle from sliding off the proximal end of the lead 400.

Turning now to FIGS. 12-14B, in at least some embodiments a kit for providing electrical stimulation of patient tissue includes the lead 400 and a lead introducer configured and arranged for facilitating insertion of the lead 400 into a patient. In at least some embodiments, the lead introducer includes a removable outer member configured and arranged to receive the lead 400 during insertion of the lead 400 into a patient.

Figure 12:
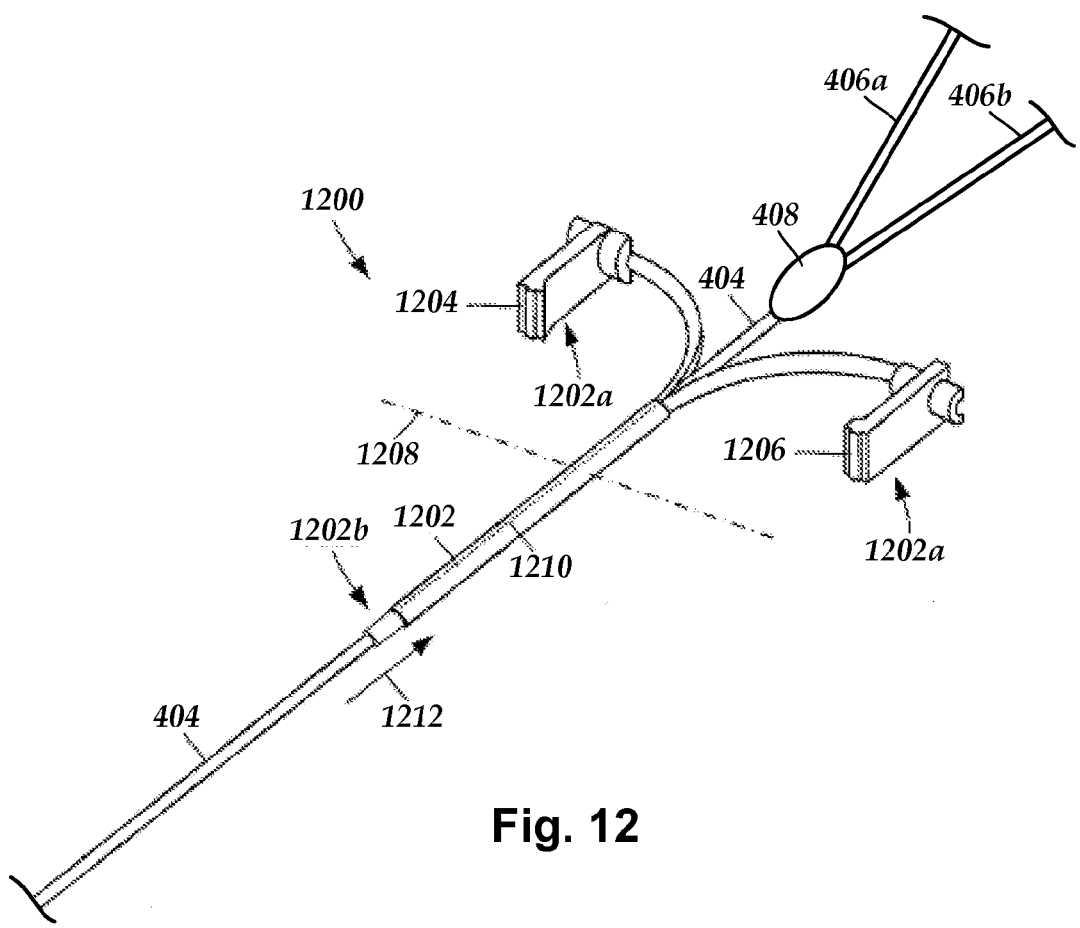
FIG. 12 is a schematic perspective view of one embodiment of a lead introducer that includes an outer member that splits to separate from a trial lead, according to the invention.

In at least some embodiments, the outer member is separatable from the trial lead by splitting apart. FIG. 12 is a schematic perspective view of one embodiment of a lead introducer 1200 that includes a outer member 1202 that splits to separate from the lead 400. The outer member 1202 includes a proximal hub 1202a having at least two pull-apart tabs 1204 and 1206.

In at least some embodiments, the outer member 1202 is formed from a flexible material suitable for implantation into a patient 1208 including, for example, fluorinated ethylene propylene, polytetrafluoroethylene, high-density polyethylene, polyetheretherketone, and the like or combinations thereof. Additionally, one or more radiopaque materials may be added including, for example, barium sulfate and bismuth subcarbonate, and the like or combinations thereof to facilitate implantation of the introducer sheath through the use of one or more medical imaging techniques, such as fluoroscopy.

In at least some embodiments, the outer member 1202 includes one or more weakened regions 1210, such as score lines or perforations, extending along at least a portion of a length of the outer member 1202 from between the at least two pull-apart tabs 1204 and 1206. In at least some embodiments, when the at least two pull-apart tabs 1204 and 1206 are separated from one another, for example, by pulling each pull-apart tab away from the other pull-apart tab(s) in directions approximately orthogonal to the outer member 1202, outer member 1202 separates along the one or more weakened regions 1210.

In at least some embodiments, outer member 1202 is separated into a plurality of longitudinal strips while pulling the outer member 1202 proximally along the lead 1200. As the outer member 1202 splits apart, the distal end 1202b of the outer member 1202 moves proximally along the lead 400 (as shown by arrow 1212), with an increasing amount of the lead 400 extending through the distal end 1202b of the outer member 1202. In at least some embodiments, an undersurface of the outer member 1202 includes a lubricious coating to facilitate the proximal movement of the outer member 1202.

Eventually, the outer member 1202 may be completely separated into two or more longitudinal strips, thereby separating completely from the lead 400 and also from the patient. In at least some embodiments, the distal ends of the outer member 1202 may be extracted from the patient as the outer member 1202 is split apart. In at least some embodiments, the outer member 1202 may be split apart without causing the lead 400 to move.

In at least some embodiments, an insertion needle includes one or more body lead elements that receive the trial lead and that separate from one another after removal of the outer member. In at least some embodiments, separation of the one or more body lead elements enables removal of the body lead elements from the patient, while the lead 400 remains within the patient. In at least some embodiments, separation of the one or more body lead elements enables removal of the one or more body lead elements from the patient without sliding the insertion needle along the proximal end of the lead 400.

In at least some embodiments, the lead introducer includes an insertion needle configured and arranged to receive the trial lead and also configured and arranged for insertion into the outer member. In at least some embodiments, the insertion needle includes at least one body lead element that defines an open channel defined along a length of the insertion needle. In at least some embodiments, when the outer member is removed from the insertion needle, the trial lead laterally separates from the insertion needle by passing through the open channel.

Figure 13A:
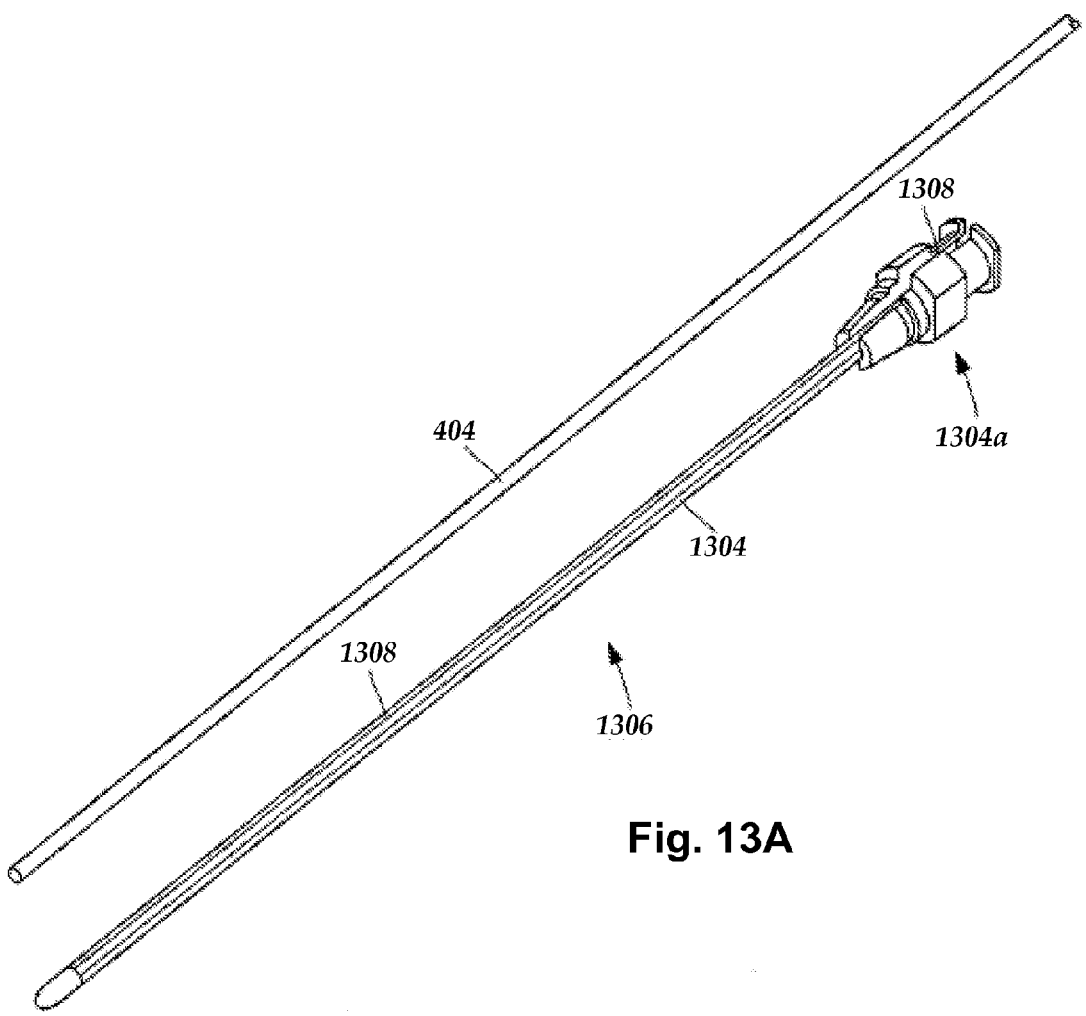
FIG. 13A is a schematic perspective view of one embodiment of a lead and a body lead element of an insertion needle, the body lead element defining an open channel extending along a length of the body lead element, the open channel configured and arranged to receive the trial lead, according to the invention.

FIG. 13A is a schematic perspective view of one embodiment of the distal lead element 404 and a body lead element 1304 of an insertion needle 1306. The body lead element 1304 defines an open channel 1308 extending along a length of the body lead element 1304. The open channel 1308 is configured and arranged to receive the trial lead. In at least some embodiments, the open channel 1308 extends substantially entirely along a length of the body lead element 1304. In at least some embodiments, the open channel 1308 extends along a proximal hub 1304a of the body lead element 1304. In at least some embodiments, the insertion needle 1306 includes one more additional body lead elements.

In at least some embodiments, the open channel 1308 is configured and arranged to receive the distal lead element 404 during insertion of the lead 400 into the patient, and separate from the distal lead element 404 during removal of the body lead element 1304. In at least some embodiments, the open channel 1308 separates from the distal lead element 404 without moving the distal lead element 404 axially relative to the body lead element 1304 of the insertion needle 1306. In at least some embodiments, the open channel 1308 separates from the distal lead element 404 by applying enough lateral force to at least one of the distal lead element 404 or the body lead element 1304 to pass the distal lead element 404 out through the open channel 1308. In at least some embodiments, the open channel 1308 has a width that is no less than a diameter of the distal lead element 404.

Figure 13B:
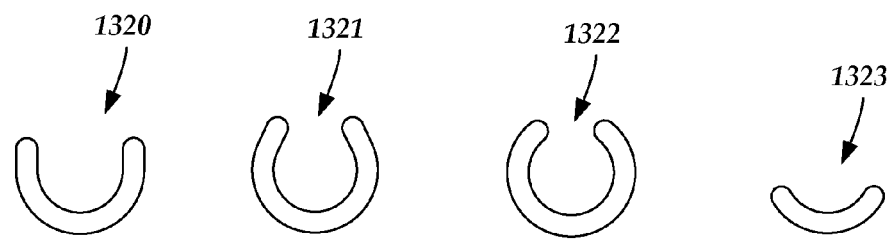
FIG. 13B is a schematic transverse cross-section al view of several exemplary embodiment s of the open channel of the body lead element of FIG. 13A, according to the invention.

FIG. 13B is a schematic transverse cross-sectional view of several different exemplary embodiments of the open channel 1308. In at least some embodiments, the portions of the body lead element 1304 along which the open channel 1308 extends have a transverse cross-sectional shape that is at least substantially U-shaped 1320. In at least some embodiments, the portions of the body lead element 1304 along which the open channel 1308 extends have a transverse cross-sectional shape that is at least substantially horseshoe-shaped 1321. In at least some embodiments, the portions of the body lead element 1304 along which the open channel 1308 extends have a transverse cross-sectional shape that is at least substantially C-shaped 1322. In at least some embodiments, the portions of body lead element 1304 along which the open channel 1308 extends have a transverse cross-sectional shape that is at least substantially arc-shaped 1323.

In at least some embodiments, the outer member 1202 may be rolled or slid along a length of the trial lead or the insertion needle. In at least some embodiments, the lead introducer includes an insertion needle formed from a plurality of body lead elements and an outer member 1202, such as heat shrink tubing, disposed over at least a portion of the insertion needle. In at least some embodiments, the insertion needle separates upon removal of the outer member. In some embodiments, the insertion needle may be separated from the trial lead when the body lead elements are partially separated from one another. In other embodiments, the insertion needle may be separated from the trial lead when the body lead elements are completely detached from one another.

Figure 14A:
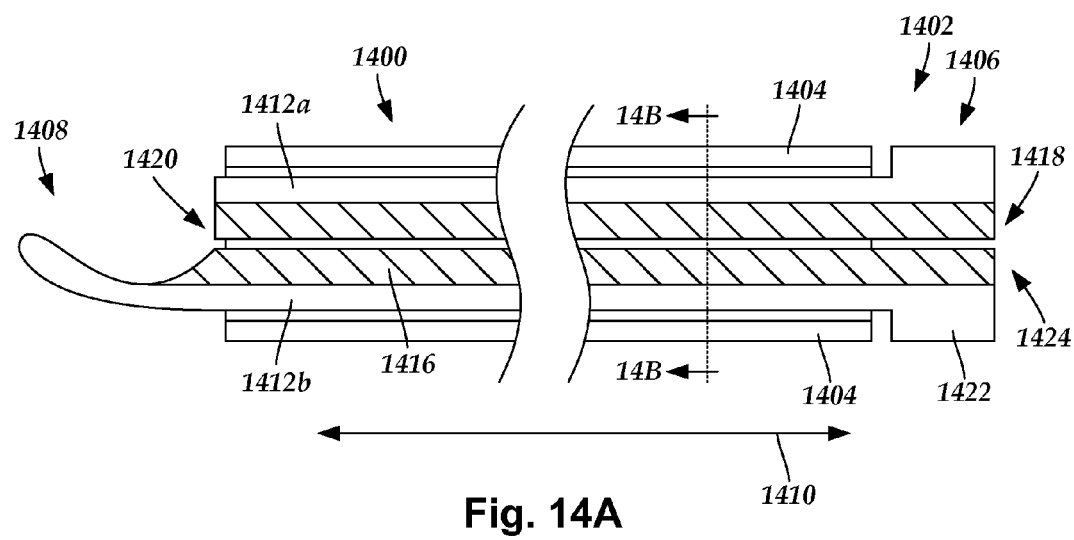
FIG. 14A is a schematic longitudinal cross-sectional view of one embodiment of a lead introducer with an outer member disposed over a split-release insertion needle, according to the invention.
Figure 14B:
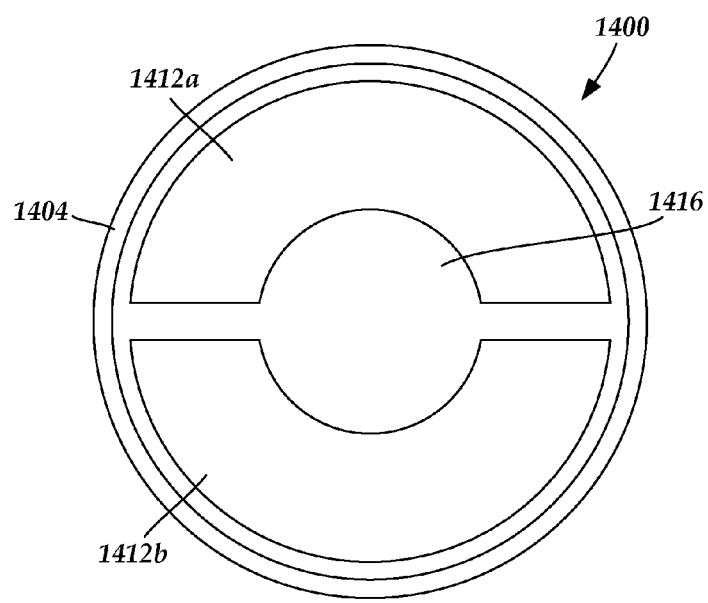
FIG. 14B is a schematic transverse cross-sectional view of one embodiment of the lead introducer of FIG. 14A, according to the invention.

FIG. 14A is a schematic longitudinal cross-sectional view of one embodiment of a lead introducer 1400 that includes an insertion needle 1402 and an outer member 1404 disposed over the insertion needle 1402. FIG. 14B is a schematic transverse cross-sectional view of the lead introducer 1400. The insertion needle 1402 includes a proximal end 1406, a distal end 1408, and a longitudinal axis 1410 (shown by a two-headed arrow). The insertion needle 1402 also includes a plurality of body lead elements 1412a and 1412b mated together to define a lumen 1416. In at least some embodiments, the body lead elements 1412a and 1412b are mated along the longitudinal axis 1410 of the insertion needle 1402. In at least some embodiments, the lumen 1416 extends along the longitudinal axis 1410. In at least some embodiments, the lumen 1416 extends along the longitudinal axis 1410 from the proximal end 1406 to the distal end 1408 of the insertion needle 1402. In at least some embodiments, the lumen 1416 extends from a proximal aperture 1418 at the proximal end 1406. In at least some embodiments, the lumen 1416 extends from a distal aperture 1420 at the distal end 1408.

In at least some embodiments, the body lead elements are mated together within the outer member 1404 such that the body lead elements 1412a and 1412b are at least partially separatable from one another when the outer member 1404 is removed. In at least some embodiments, the body lead elements 1412a and 1412b at least partially separate from one another along a longitudinal axis of the insertion needle 1402. In at least some embodiments, the body lead elements 1412a and 1412b separate from one another such that at least some of the plurality of body lead elements 1412a and 1412b remain coupled together. In at least some embodiments, the body lead elements 1412a and 1412b separate from one another such that at least some of the body lead elements 1412a and 1412b completely detach from one another. When the body lead elements 1412a and 1412b are separated (either partially or fully) from one another, the body lead elements 1412a and 1412b may be removed from the patient, leaving the lead 400 in place. In at least some embodiments, when the body lead elements 1412a and 1412b are separated (either partially or fully) from one another, the body lead elements 1412a and 1412b may be removed from the patient without sliding the insertion needle 1402 off the proximal end of the lead 400 through the lumen of the lead introducer 1400.

The outer member 1404 may be formed from any thermoplastic material suitable for implantation including, for example, polyester, polyolefin, one or more fluoropolymers (such as fluorinated ethylene propylene, polytetrafluoroethylene, polyvinylidene fluoride, or the like or combinations thereof), polyvinyl chloride, polychloroprene, silicone elastomer, or the like or combinations thereof.

In at least some embodiments, the outer member 1404 is disposed over at least a portion of an outer surface of the insertion needle 1402. In at least some embodiments, the outer member 1404 is disposed substantially entirely over the outer surface of the insertion needle 1402 distal to the proximal hub 1422. In at least some embodiments, the outer member 1404 is disposed entirely over the outer surface of the insertion needle 1402. In at least some embodiments, the outer member 1404 forms a watertight seal along the lumen 1416 of the insertion needle 1402.

In at least some embodiments, once the outer member 1404 is rolled or slid off the proximal end 1406 of the insertion needle 1402, the outer member 1404 can be slid or rolled over the junction 408. In at least some embodiments, the outer member 1404 can be stretched to pass over the junction 408.

In at least some embodiments, the outer member 1404 can be removed by cutting the outer member 1404 along the longitudinal axis 1410 of the outer member 1404. In at least some embodiments, the outer member 1404 can remain encircling the proximal end of the lead 400, external to the patient.

Figure 15:
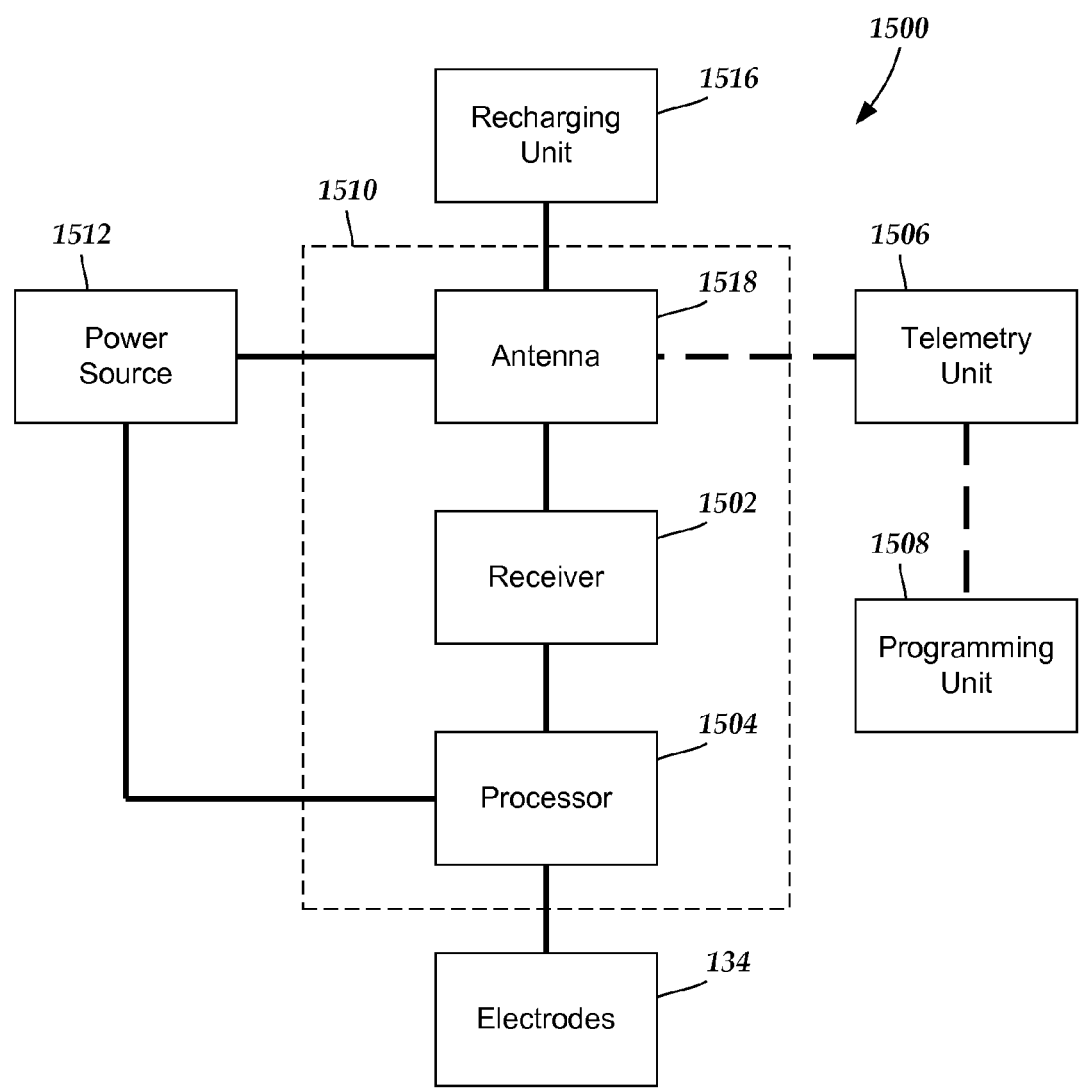
FIG. 15 is a schematic overview of one embodiment of components of a stimulation system, including an electronic subassembly disposed within a control module, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, power source 1512, antenna 1518, receiver 1502, and processor 1504) of the electrical stimulation system can be positioned on one or more circuit arrangements or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 may select which electrode(s) are cathodes and which electrode(s) are anodes. In some embodiments, the processor 1504 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by a programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include an antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead for providing electrical stimulation of patient tissue, the lead comprising;
   a distal lead element comprising
      a plurality of electrodes disposed on the distal lead element, and
      a plurality of conductive wires coupled to the plurality of electrodes and extending along a longitudinal axis of the distal lead element;
   at least two proximal lead elements, each of the at least two proximal lead elements comprising
      a plurality of terminals disposed on the proximal lead element, and
      a plurality of conductive wires coupled to the plurality of terminals and extending along a longitudinal axis of the proximal lead element; and
   a junction coupling the distal lead element to each of the at least two proximal lead elements, the junction comprising a circuit arrangement electrically coupling each of the conductive wires of the distal lead element to at least one of the conductive Wires of at least one of the at least two proximal lead elements, wherein the circuit arrangement comprises a flexible substrate and a plurality of conductive junction elements at least partially disposed on the substrate.

2. The lead of claim 1, wherein the plurality of conductive junction elements are each coupled to at least one non-conductive spine.

3. The lead of claim 1, wherein the circuit arrangement comprises a flex circuit.

4. The lead of claim 1, wherein the circuit arrangement is rolled up within the junction.

5. The lead of claim 1, wherein the circuit arrangement is folded up within the junction.

6. The lead of claim 1, wherein a first lumen is defined in the distal lead element and a second lumen is defined in a one of the proximal lead elements.

7. The lead of claim 6, wherein the junction farther comprises a transition tube coupling the first lumen to the second lumen to form a continuous passage between the first lumen and the second lumen configured and arranged to receive a stylet.

8. The lead of claim 7, wherein the circuit arrangement is rolled up around the transition tube.

9. The lead of claim 1, wherein a first one of the proximal lead elements has a length that is different from a second one of the at least two proximal lead elements.

10. The lead of claim 1, wherein the plurality of conductive junction elements comprise at least one conductive tracing.

11. The lead of claim 1, wherein the plurality of conductive junction elements comprise at least one conductive strut.

12. An electrical stimulating system comprising;
the lead of claim 1;
at least one control module configured and arranged to electrically couple to each of the proximal lead elements, each of the at least one control module comprising
a housing, and
an electronic subassembly disposed in the housing; and
a connector for receiving at least one of the at least two proximal lead elements, the connector having a proximal end, a distal end, and a length, the connector configured and arranged to receive at least one of the two proximal lead elements, the connector comprising
a connector housing defining at least one port at the distal end of the connector, the at least one port configured and arranged for receiving at least one of the two proximal lead elements, and
a plurality of connector contacts disposed in the connector housing, the connector contacts configured and arranged to couple to at least one of the plurality of terminals disposed on each of the at least one of the two proximal lead elements.

13. A kit for providing electrical stimulation of patient tissue during a trial stimulation, the kit comprising:
the lead of claim 1; and
a lead introducer for facilitating insertion of the trial stimulation lead into the patient, the lead introducer comprising
an outer member configured and arranged for insertion into the patient, and
an insertion needle configured and arranged for insertion into the outer member, the insertion needle also configured and arranged to receive the distal lead element.

14. The kit of claim 13, further comprising a stylet for facilitating guidance of the electrodes to a target stimulation region within the patient, the stylet configured and arranged for insertion into the first lumen of the distal lead clement and the second lumen of one of the at least two proximal lead elements.

15. The kit of claim 13, wherein the outer member is configured and arranged to divide into at least two parts for removal of the outer member from the distal lead element upon insertion of the lead into the patient.

16. The kit of claim 13, wherein the insertion needle defines an open channel configured and arranged to receive at least a portion of the distal lead element.

17. The kit of claim 13, wherein the insertion needle comprises a plurality of body lead elements configured and arranged to at least partially separate from one another upon removal of the outer member.

18. A method of fabricating a lead, the method comprising
providing a plurality of electrodes on a distal lead element;
providing a plurality of first terminals on a first proximal lead element;
providing a plurality of second terminals on a second proximal element;
electrically coupling a plurality of conductive wires to the plurality of electrodes and extending the conductive wires along a longitudinal length of the distal lead element;
electrically coupling a plurality of conductive wires to the plurality of first terminals and extending the conductive wires along a longitudinal length of the first proximal lead element;
electrically coupling a plurality of conductive wires to the plurality of second terminals and extending the conductive wires along a longitudinal length of the second proximal lead element;
electrically coupling each of the conductive wires of the distal lead element to at least one of the conductive wires of either of the first proximal lead element or the second proximal lead element using a circuit arrangement;
rolling up the circuit arrangement and inserting the circuit arrangement into a junction; and
coupling the distal lead element, the first proximal lead element and the second proximal lead element to the junction.

19. The method of claim 18, wherein rolling up the circuit arrangement comprises rolling up the circuit arrangement around a transition tube coupled at one end to a lumen defined in the distal lead element and. coupled at another end to a lumen defined in the first proximal lead element.

20. A method of fabricating a lead, the method comprising
providing a plurality of electrodes on a distal lead element;
providing a plurality of first terminals on a first proximal lead element;
providing a plurality of second terminals on a second proximal element;
electrically coupling a plurality of conductive wires to the plurality of electrodes and extending the conductive wires along a longitudinal length of the distal lead element;
electrically coupling a plurality of conductive wires to the plurality of first terminals and extending the conductive wires along a longitudinal length of the first proximal lead element;
electrically coupling a plurality of conductive wires to the plurality of second terminals and extending conductive wires akin longitudinal length of the second proximal lead element;
electrically coupling each of the conductive wires of the distal lead element to at least one of the conductive, wires of either of the first proximal lead element or the second proximal lead element using a circuit arrangement;

inserting the circuit arrangement into a junction;

coupling the distal lead element, the first proximal lead element and the second proximal lead element to the junction; and center-less grinding at least one of the distal lead element, the first proximal lead element, or the second proximal lead element prior to electrically coupling each of the conductive wires of the distal lead element to at least one of the conductive wires of either of the first proximal lead element or the, second proximal lead element using a circuit arrangement.

* * * * *